United States Patent [19]
Zimmerman et al.

[11] Patent Number: 5,922,929
[45] Date of Patent: Jul. 13, 1999

[54] THERMOTOLERANCE ENHANCING PROTEIN

[75] Inventors: J. Lynn Zimmerman, Marriottsville; Janet P. Slovin, Silver Spring; Mukesh K. Malik, Ellicott City, all of Md.

[73] Assignee: University of Maryland at Baltimore County, Baltimore, Md.

[21] Appl. No.: 08/850,588

[22] Filed: May 2, 1997

[51] Int. Cl.[6] .............................. C12N 5/04; C12N 12/29; A01H 5/00
[52] U.S. Cl. ......................... 800/278; 800/278; 800/289; 800/317.4; 536/23.6; 435/419
[58] Field of Search .......................... 536/23.6; 435/419; 800/205, DIG. 44, 278, 289, 317.4

[56] References Cited

PUBLICATIONS

Matzke and Matzke. Plant Physiol. 1995. vol. 107: 679–685.
Finnegan and McElory, 1994. Bio/Technology. vol. 12: 883–888.
Napoli et al. The Plant Cell. 1989. vol. 2: 279–289.
Carvalho et al. The EMBO Journal. 1992. vol. 11: 5995–5602.
An et al. Plant Physiol. 1986. vol. 81: 301–305.
Vierling. Ann. rev. of Plant Physiol. 1991. vol. 42: 579–620.
Darwish et al. Plant Molecular Biology. 1991. vol. 16: 729–731.

*Primary Examiner*—Douglas W. Robinson
*Assistant Examiner*—Ousama M-Faiz Zaghmout
*Attorney, Agent, or Firm*—Benjamin Aaron Adler

[57] ABSTRACT

All organisms respond to elevated temperature by specifically inducing the expression of a set of new proteins; the "heat shock proteins" or "Hsps." Although this response has been known for over thirty years, the specific role of individual heat shock proteins in the overall response is still largely unknown. All organisms have a basal level of thermotolerance—an organism-specific temperature threshold above which they die. The advantage to increased thermotolerance in a plant is clear—increased thermotolerance improves crop yield in particularly hot growing seasons, and expands the geographic area where a particular crop can be grown. The present invention provides a method of increasing thermotolerance in plants comprising transforming plant cells with a vector which over-expresses the carrot Hsp17.7 gene. This is the first demonstration of enhancement of plant thermotolerance through the overexpression of a low molecular weight heat shock protein. Additionally, the fact that the enhanced thermotolerance effect can be transferred from one species (carrot) to a completely unrelated species (tomato) is highly significant, as it demonstrates that this gene construct is able to confer enhanced thermotolerance to a wide range of plant species.

11 Claims, 4 Drawing Sheets

THERMOTOLERANCE ENHANCING PROTEIN

BACKGROUND OF THE INVENTION

This invention was produced in part using funds obtained through a grant from the USDA. Consequently, the federal government has certain rights in this invention.

1. Field of the Invention

The present invention relates generally to the molecular biology of plants. Specifically, the present invention relates to a method of enhancing thermotolerance in a plant by transforming the plant with a carrot heat shock protein Hsp17.7, and the resulting thermotolerant plant.

2. Description of the Related Art

All organisms respond to elevated temperature by specifically inducing the expression of a set of new proteins; the "heat shock proteins" or "Hsps." Although this response has been known for over thirty years, the specific role of individual heat shock proteins in the overall response is still largely unknown. Those Hsps that have been attributed a function appear to function as molecular chaperones—enabling protein folding, preventing denaturation of other proteins, or mediating proteolysis. This role, however, has only been demonstrated for a few of the many known of Hsps, and the function of the others remains unknown. Moreover, it is not known which of the heat shock proteins are essential for the overall heat shock response except in the few cases described below.

All organisms have a basal level of thermotolerance—an organism-specific temperature threshold above which they die. Basal levels of thermotolerance are probably determined by a variety of factors, including, e.g., membrane composition and the innate thermal stability of enzymes involved in normal cellular processes. An additional level of thermotolerance can be acquired by exposure of a n organism to sublethal high temperatures prior to exposure to the normally lethal temperature. Such "acquired thermotolerance" is believed to result from the production of Hsps in response to the sublethal high temperature exposure.

Heat shock proteins have been categorized by size and DNA sequence into families that are evolutionarily conserved. These families include the Hsp90/clp protein family, the Hsp70s, the Hsp 60s, and a variable class of low molecular weight proteins that range from 20–25 kilodaltons in most animals, and to 14–20 kilodaltons in most plants. It is within this low molecular weight class that the plant and animal heat shock proteins differ most strikingly. In animals there are generally one to a few low molecular weight (LMW) Hsps (e.g., one in chicken and yeast, four in fruit flies), whereas in plants there are generally 20–30 different LMW Hsps. It is not understood why plants have so many LMW Hsps and almost nothing is known about the individual functions of these LMW Hsps.

The LMW Hsps of plants are encoded by approximately six gene families with significant homology among family members. The LMW Hsps have been placed into five classes. Class I and Class II Hsps consist of distinct cytoplasmically-localized proteins. Two other classes, the chloroplast and endoplasmic reticulum-localized proteins, have transit sequences consistent with their localization. Recently, a mitochondrial Hsp was described and it too has a transit sequence, but it represents a separate class because it lacks the distinct conserved regions at the amino termini that the other transported classes contain. Vierling, E., *Annu. Rev. Plant Physiol. Plant Mol. Biol.* 42:579–620 (1991), lists a small number of additional proteins that do not fit into these classes, suggesting that as studies continue, it will be possible to define other classes.

All of the LMW Hsps are distinguished by the conserved carboxy termini which are highly homologous to the aB-crystallin structural protein of the eye lens. α-B-crystallin is itself capable of acting as a molecular chaperone, and all LMW Hsps have been shown to exhibit chaperone activities in in vitro experiments. Their role in cells has not yet been demonstrated.

While it might be assumed that the LMW Hsps play a role in thermotolerance because of the correlation of their abundant synthesis with exposure to increased temperature, earlier work with yeast had suggested that they are unimportant for the development of thermotolerance, as elimination of the single yeast LMW Hsp had no effect on thermotolerance. In addition, in Drosophila cells, the use of antisense technology caused the specific decrease in the synthesis of the Hsp26 protein, but the decrease had no effect on thermotolerance. In plants, transgenic tobacco cells expressing a constituitively expressed antisense version of the soybean Hsp17.9 gene showed perturbations in the mRNA accumulation pattern, but no data were presented to indicate whether there was an effect on thermotolerance in the single plant examined.

In addition to being induced by temperature stress, many Hsps, including those in the LMW class, can be induced by other stresses such as exposure to arsenite, ethanol, heavy metals, amino acid analogues (Lee, Y.-R., et al., *Plant Physio.* 110:241–48 (1996); and Nover, L., (ed.) *Heat Shock Response*. CRC Press (1990).) and water stress (Almoguera C. et al., *The Plant Journal* 4(6):947–58 (1993)). In addition, increasing numbers of Hsps and Hsp-homologues are being found to be regulated in developmental and tissue-specific ways (see, e.g., Almoguera, C. and J. Jordano, *Plant Molecular Biol.* 19:781–92 (1992); Apuya, N. R. and J. L. Zimmerman, *The Plant Cell*, 4:657–65 (1992); Cordewener, J. H. G., et al., *Planta* 196:747–52 (1995); Pitto, L., Plant Mol Biol. 2:231–37 (1983); and Zimmerman, J. L., et al., *Plant Cell* 1:1137–1140 (1989)). Proteins with highly conserved sequences related to Hsps (Hsp cognates), may be expressed in non-stressed normal cells, but are not induced by thermal stress.

The heat shock response of carrot cells has been characterized, and it has been found that they exhibit a very characteristic "higher plant" heat shock response (Heikkila J. J. *Dev. Genetics*, 14:1–5 (1993)). Two dimensional PAGE analysis of newly synthesized proteins revealed carrot cell cultures produce about 16 LMW Hsps as well as the characteristic larger proteins. These studies showed that the various Hsps are synthesized asynchronously, both with respect to time following the heat shock, and in response to different temperatures. Typically the larger heat shock proteins appear before the smaller ones, and the 17kDa group appears at 33° C. but the 19 kDa group is not detected until 35° C.

Three genes for carrot LMW Hsps have been isolated and characterized (Darwish, K. Heat Shock Gene Expression in Callus Suspension Cells and Somatic Embryos or Carrot, PhD Thesis, U. of Maryland (1989); and Darwish, K., et al., *Plant Molec. Biol*, 16:72931 (1991)). In hybrid selection experiments, one of these clones, Hsp 17.7, selected a small family of mRNAs, one of which translated into a major spot on 2 D gels at 17.5 kDa. The predicted amino acid sequence of the three clones revealed that they all belong to Class I. They have the very highly-conserved carboxy terminus typical of all LMW Hsps, have 92% nucleotide identity between their coding sequences, and have 80% nucleotide identity to a soybean clone GMHsp17.5M (Darwish, K. Heat Shock Gene Expression in Callus Suspension Cells and Somatic Embryos or Carrot, PhD Thesis, U. of Maryland (1989); and Darwish, K, et al., *Plant Molec. Biol*, 16:729–31 (1991)). These genes, including Hsp17.7, were analyzed in the carrot system, as a "typical example" of LMW Hsps in higher plants. Studies of heat shock gene regulation during somatic embryo development revealed that when carrot cell cultures undergo somatic embryogenesis, the regulation of heat shock gene expression shifted from the level of transcription to translation when development reaches the globular stage (Zimmerman, J. L., et al., *J. Plant Cell*, 1:1137–1146 (1989)). The Hsp17.7 gene was subsequently selected for studies on the consequences of over-expression of a LMW Hsp on plant cell thermotolerance.

The prior art is deficient in a non-species specific method of enhancing thermotolerance. The present invention fulfills this long-standing need and desire in the art.

SUMMARY OF THE INVENTION

One object of the present invention is to provide a method of enhancing thermotolerance in a plant, comprising the steps of: transforming a cell or organ of the plant with a low molecular weight heat shock protein gene from carrot contained in a vector to produce a transformed cell or organ, wherein the vector further contains a promoter capable of overexpression of the low molecular weight heat shock protein gene and other sequences appropriate for successful transcription, translation and expression of the low molecular weight heat shock protein gene; and growing said cell or organ into a mature plant or organ.

In an embodiment of the present invention, there is provided a method of enhancing thermotolerance in a plant, comprising the steps of: transforming a cell or organ of the plant with low molecular weight heat shock protein gene Hsp 17.7 from carrot contained in a vector to produce a transformed cell or organ, wherein the vector further contains a promoter capable of overexpression of the low molecular weight heat shock protein gene and other sequences appropriate for successful transcription, translation and expression of the low molecular weight heat shock protein gene; and growing said cell into a mature plant. Other embodiments include using the CaMV 35S promoter and a selection gene in the vector of the present invention and transforming carrot and tomato tissue.

A further aspect of the present invention is to provide a plant transformed with and expressing a heterologous low molecular weight heat shock protein gene. In an embodiment of this aspect of the invention, there is provided a plant transformed with and expressing a Hsp 17.7 gene from carrot. In addition, the transcription of the Hsp 17.7 gene from carrot may be controlled by a promoter capable of overexpression of said Hsp 17.7 gene from carrot. A preferred embodiment of the transformed plant is one that has been transformed with a vector containing a selection gene and a sequence to allow replication in bacteria and sequences to facilitate integration into a genome of said plant.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

Figure 1:
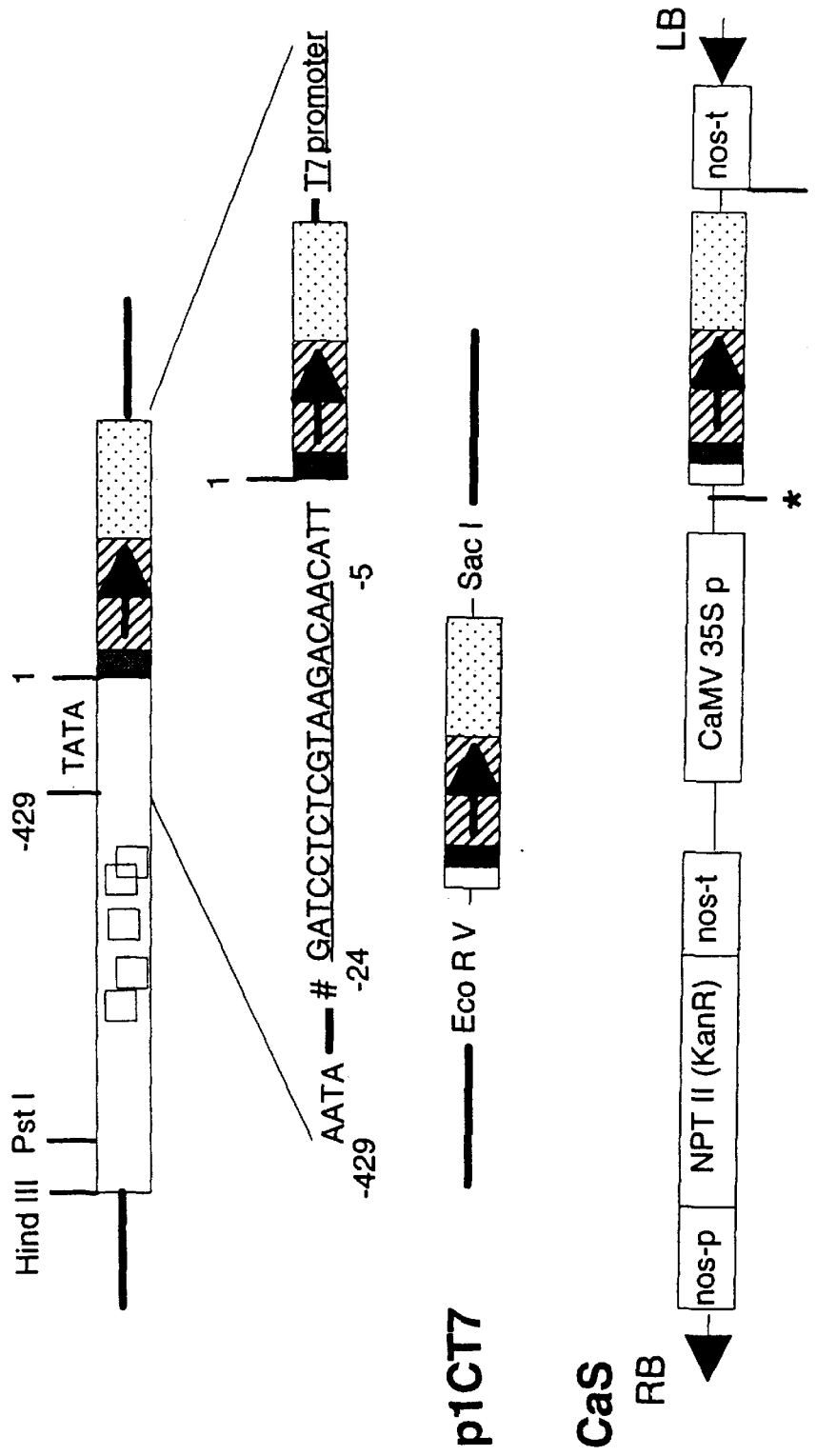
FIG. 1 shows the construction of the pCaS plasmid. Note the 1 kb EcoR V—Sac I fragment of plasmid p1CT7 (containing the Hsp17.7 coding sequence) was purified and ligated with the 35S promoter. Thus, the pCaS plasmid has the CaMV 35S promoter upstream (5') of the Hsp17.7 gene, followed by the nopaline syntase (nos-t) polyadenylation signal. "*" denotes where the vector and the inset were joined by blunt end ligation of Sma I and EcoR V, respectively. To provide a marker for selection in carrot and tomato transformation, the plasmid pCaS contains a kanamycin resistance gene (NPT II) driven by the nopaline synthase gene promoter (nos-p; part of the pBI121 vector construct).

It will be apparent to one skilled in the art that various substitutions and modifications may be made to the invention disclosed herein without departing from the scope and spirit of the invention.

As used herein, the term "heat shock protein" refers to any protein whose synthesis is enhanced when an organism or its cells are exposed to an increased temperature for that species; typically 5–15° C. above the normal growth temperature.

As used herein, the term "low molecular weight heat shock protein" refers to those heat shock proteins that are between 12 and 30 kilodaltons (kDa) in size.

As used herein, the term "Hsp 17.7" refers to the heat shock protein encoded by the carrot Hsp17.7 gene.

As used herein, the term "thermotolerance" refers to the ability of a cell to survive exposure to temperatures above its normal growth temperature.

As used herein the term "basal thermotolerance" refers to the maximum temperature to which an organism or cell can survive when the shift to that temperature is rapid.

As used herein the term "acquired thermotolerance" refers to the increase in thermotolerance that results from a prior (pre) exposure to a sublethal heat shock temperature.

As used herein, the term "transgenic cell line" or "transgenic culture" refers to a cell or culture that has stably incorporated added DNA sequences into its genome after deliberate introduction of that DNA into the cell.

As used herein, the term "callus" refers to undifferentiated plant cells growing in culture medium.

As used herein, the term "CaMV 35S promoter" refers to the promoter of the 35S RNA gene of Cauliflower Mosaic Virus.

The present invention is directed to a method of enhancing thermotolerance in a plant, comprising the steps of: transforming a cell or organ of the plant with a low molecular weight heat shock protein gene from carrot contained in a vector to produce a transformed cell or organ, wherein the vector further contains a promoter capable of overexpression of the low molecular weight heat shock protein gene and other sequences appropriate for successful transcription, translation and expression of the low molecular weight heat shock protein gene; and growing said callus into a mature plant.

It is additionally contemplated to provide a method of enhancing thermotolerance in a plant, comprising the steps of: transforming a cell or organ of the plant with low molecular weight heat shock protein gene Hsp 17.7 from carrot contained in a vector to produce a transformed cell or organ, wherein the vector further contains a promoter capable of overexpression of the low molecular weight heat shock protein gene and other sequences appropriate for successful transcription, translation and expression of the low molecular weight heat shock protein gene; and growing said cell into a mature plant. Other embodiments include using the CaMV 35S promoter and a selection gene in the vector of the present invention and transforming carrot and tomato tissue.

Further, the present invention provides a plant transformed with and expressing a heterologous low molecular weight heat shock protein gene. In an embodiment of this aspect of the invention, there is provided a plant transformed with and expressing a Hsp 17.7 gene from carrot. In addition, the transcription of the Hsp 17.7 gene from carrot may be controlled by a promoter capable of overexpression of said Hsp 17.7 gene from carrot. A preferred embodiment of the transformed plant is one that has been transformed with a vector containing a selection gene and a sequence to allow replication in bacteria and sequences to facilitate integration into a genome of said plant.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). In addition, the following references are particularly helpful in describing molecular biological techniques used for plants: "Plant Molecular Biology Manual" Gelvin, S. B. and Schilperoort, R. A. eds. Kluwer Academic Publishers, Dordrecht, (1988); and "Plant Molecular Biology LabFax" Croy, R. R. D, ed. Bios Scientific Publishers, Academic Press, Oxford. (1993).

Therefore, if appearing herein, the following terms shall have the definitions set out below.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A "vector" is a replicon, such as plasmid, phage, cosmid, or virus to which another DNA or RNA segment may be attached so as to bring about the replication of the attached segment. Specialized vectors were used herein, containing various promoters, polyadenylation signals, genes for selection, etc. Basically, a vector for use in the present invention contains: (1) a sequence to allow replication in bacteria; (2) sequences to facilitate integration into the plant genome (e.g., the right and left border sequences of Agrobacterium T-DNA); (3) a gene encoding a selectable marker, for example, encoding antibiotic or herbicide resistance, to be expressed in plant cells and used to select transformed cells (e.g., gene for kanamycin resistance, hygromycin resistance, or Basta resistance); (4) the gene of interest controlled by an active promoter which is expressed either constitutively (e.g., CaMv 35S promoter, nopaline synthase promoter, or actin promoter) or in a tissue- or developmentally-specific manner (e.g., E8 promoter for fruit expression or the Gea8 promoter for expression in embryos).

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (3' direction) to include the minimum number of bases or elements necessary to initiate transcription at levels detectable above background. Within the promoter sequence will be found a transcription initiation site (conveniently defined b y mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

A "selection gene" refers to a gene that enables the discrimination of cells displaying a required phenotype upon implementation of certain conditions. For example, the growth of bacteria in medium containing antibiotics to select for the bacterial cells containing antibiotic resistance genes.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Transformation of carrot cell cultures were produced as described by Thomas et al. (1989), although the following other methods could be used: leaf disc transformation, particle bombardment of leaf pieces, or vacuum infiltration. Transformation of tomato cell cultures was performed by a modification of the method of McCormick, et al., *Plant Cell Rep.* 5:81–84 (1986).

A "heterologous" region of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

Thermotolerance of carrot plants was assayed according to the protocol of Yeh et al. (1994), although other methods known in the art would be appropriate as well. Thermotolerance of tomato plants was assayed according to Binelli, G. and Mascarenhas, J. P., *Developmental Genetics* 11:294–298 (1990), who cite 'the electrolyte leakage test' of Onwueme, *J. Agri. Sci.* 92:527–536 (1979) as modified by Chen, H.-H., et al., *Crop Sci.* 22:719–725 (1982); though one skilled in the art would recognize that the following methods, among others, can be used as well: abscission of reproductive structures in response to increased temperatures (Roberts J. A., et al., *Planta* 160: 159–163 (1984)); fruit set and pollination (Rudich, J., et al., *Bot. Gaz.* 138:448–452) (1977); and TTC reduction (Caldwell, C. R., *Plant Physiology* 101:939–945 (1993)).

The advantage to increased thermotolerance in a plant is clear. Increased thermotolerance improves crop yield in particularly hot growing seasons, and expands the geographic area where a particular crop can be grown. For example, several important developmental events in carrot and tomato have been shown to be particularly sensitive to heat. Two important heat sensitive processes that can have a significantly negative impact on crop yield are flower drop and embryo development. These processes are a particular focus for analysis of the development of the transgenic tomato and carrot plants respectively, and for other plants in general.

The following examples are given for the purpose of illustrating various embodiments of the invention and are not meant to limit the present invention in any fashion:

EXAMPLE 1
Carrot Cell Cultures:

Callus suspension cell cultures were initiated from hypocotyls of carrot seedlings (*Daucus carota* L. cv. Danvers Half-Long) as described in Zimmerman et al. (1989). Cultures were maintained in liquid MS$^+$ medium containing Murashige and Skoog salts (Sigma) supplemented with 5 mg/L 2,4-D and 3% (w/v) sucrose. Transgenic cell lines were maintained in the same media with the addition of kanamycin (100 mg/L) and carbenicillin (400 mg/L), except where indicated.

EXAMPLE 2
Construction of Plasmid pBICaS:

To facilitate cloning of the heat shock protein gene Hsp17.7 in a plant expression vector, plasmid DNA from pXB22 clone was isolated. Plasmid pXB22 contains the Hsp17.7 gene. The sequence of the gene was reported by Darwish, K., et al., Plant Mol Biol. 16:729–31 (1991). To generate a suitable fragment for subcloning, polymerase chain reaction (PCR) was performed on the pXB22 plasmid DNA. The primers used were GATCCTCTCTCGTAAGA-CAA (SEQ ID NO. 1) encoding the Hsp17.7 sequence from bases −24 to −5 (+1=first nucleotide of the transcript) of pXB22 plasmid clone and T7 promoter primer sequence. The 1 kb PCR-generated fragment was subcloned in PCR II vector (Invitrogen, San Diego, Calif.) and transformation was done according to the manufacturer's directions. Several positive colonies were selected for further restriction enzyme mapping to determine the orientation of the inserted DNA. The correct clone was identified in which the Hsp17.7 gene is oriented such that isolation as an EcoR V/Sac I fragment will allow its transcription into a sense RNA after ligation into compatible sites of the plant expression vector (pBI 121); this clone was called p1CT7.

The heat shock over-expressing plasmid, pCaS, was made by cloning the Hsp17.7 gene into the pBI121 plasmid backbone. Plasmid pBI121 (Clontech, Palo Alto, Calif.) was digested with restriction enzymes Sma I and Sac I, to remove the β-glucuronidase (GUS) gene (note: SacId and SstI are isoschizomers). The remaining 11.1 kb fragment of pBI121 plasmid includes the CaMV 35S promoter. The 1 kb EcoR V—Sac I fragment of plasmid p1CT7 (containing the Hsp17.7 coding sequence) was purified and ligated with the 35S promoter and transformed into *E. Coli* DH5-α. Thus, the pCaS plasmid has the CaMV 35S promoter upstream (5') of the Hsp17.7 gene, followed by the nopaline synthase (nos-t) polyadenylation signal (FIG. 1). To provide a marker for selection in carrot and tomato transformation, the plasmid pCaS contains a kanamycin resistance gene (NPT II) driven by the nopaline synthase gene promoter (nos-p; part of the pBI121 vector construct).

The pCaS and vector pBI101.2 (Clontech, Palo Alto, Calif.) were transferred to Agrobacterium tumefaciens LBA4404 by triparental mating (Ausubel, 1986).

EXAMPLE 3
Production of Transgenic Carrot Cultures:

Transformed carrot cell cultures were produced as described by Thomas, J. C. et al., *Plant Cell Rep.* 8:354–57 (1989). Sections of hypocotyls from one-week-old sterile germinated seedlings were incubated in MS$^+$ liquid medium in the dark for two days, then incubated for 5 minutes with Agrobacterium containing the pCaS or vector control constructs. Following co-cultivation, the sections were dried briefly (5 minutes) in air, grown for 2–3 days in liquid MS$^+$ at room temperature, then transferred to MS$^+$ agar plates containing kanamycin (100 mg/L) and carbenicillin (400 mg/L) and allowed to proliferate callus in the dark. Calli which grew to 0.5 cm in diameter were used to initiate suspension cultures. Genomic DNA gel blots were analyzed to positively identify transgenic lines and to obtain insertion copy number using the NPTII sequence a probe to avoid hybridization to the endogenous carrot sequences.

EXAMPLE 4

Production of Transgenic Tomatoes:

The axenic tissue was prepared by placing approximately 50 tomato seeds in a 50 ml conical tube containing 45 ml of distilled $H_2O$, 5 ml bleach, and about 51 µl dishwashing detergent. The closed tube was shaken for 10 minutes, and the seeds were allowed to settle to the bottom. Most of the liquid and the floating seeds were poured off in a sterile hood. The tube was then refilled with sterile water, again the tube was shaken and the liquid poured off. This process was repeated until no more soap bubbles appeared when the tube was shaken (at least 5 times). Next, the seeds were poured onto a sterile piece of nylon window screen (sterilized by soaking in 10% bleach solution) and rinsed several times with more water. The seeds were placed into sterile Magenta boxes containing solidified water agar (0.8% bacto agar, water), and the lid of each box was sealed with parafilm. The box was placed in the light for seeds to germinate. Seedlings are ready for transformation when they are upright, with their cotyledons (seed leaves) opened wide and green. This process takes about eight to twelve days. The seedlings should be used before most of the seedlings sprout their first set of true leaves.

Transformation was performed in the following way: One to two days before the transformation, 5 ml of liquid LB or YM media with appropriate antibiotics was placed in a sterile culture tube, and vortexed gently. The media was then innoculated with the appropriate strain of Agrobacteria. Incubation was at 28° C. with shaking at 250 rpm. The resulting culture had strands of bacterial "mucus" swirling around.

Plant material was prepared by preincubating cotyledons on callus media for one day prior to exposure to the bacteria. Using sterile technique, five seedlings at a time were pulled from the magenta box and placed in a petri dish containing sufficient liquid MSO media to cover the bottom of the dish. Using a sterile scalpel, the tips of the cotyledons were cut off while in they were in the liquid. The remaining seedling was discarded. The cut cotyledons were placed onto a plate containing callus medium with the cut edges touching the media. Cotyledons cut in this manner can be used up to three days later for sucessful transformation Co-cultivation was performed by gently pelletting the Agrobacterium culture in a 50 ml conical centrifuge tube at room temperature and resuspending the cells in 50 ml of MSO. The resuspended cells were poured into a deep petri dish and the preincubated cotyledons were placed into the solution. The dish was sealed with parafilm and placed on a shaker, gently swirling, for 30 minutes. The excess bacterial culture was removed from each cotyledon by blotting on sterile filter paper and the cotyledons were placed back onto the callus plate, abaxial side up. The next day (about 24 hours later), all the cotyledons were tranferred to Shoot media plates containing selecting antibiotics and antibiotics to minimize Agrobacterium growth. Shoots appeared within 3 weeks. Once the shoots appeared, the cotyledon pieces were then transferred to Shoot E media.

As the shoots reached 3–7 cm in height and appeared to have an apex, they were ransferred to rooting media (Root Media or MS$^+$ Media). When the shoots on rooting media developed roots, they were transferred to soilless potting mixture wetted with hydroponic media and protected from dessication by wrapping the pot with a tent of plastic wrap. The plants were placed back in the growth chamber or tissue culture room under lights. The plantlets were checked each day. When the plant suddenly seemed to double in height in one day, the wrap was removed. The tomato plants were kept in the chamber for a few more days to be sure it was adapting well, then it was transferred to the greenhouse mist bench.

The following media were used:

Callus media:
  1× MS basal salt media (Sigma M-5524)
  3% sucrose
  100 mg/L inositol (myo-inositol)
  0.2 mg/L 2,4-D
  200 mg/L $KH_2PO_4$
  Mix well
  pH to 5.7
  0.8% phytoagar
  Autoclave (20 min for a liter, and use slow exhaust)
  After cooling to ~45° C., add,
  1.5 mg/L thiamin
  0.2 mg/L kinetin,
  Pour into standard petri dishes and store at 4° C.

Shoot media:
  1× MS basal salt media
  3% sucrose
  Mix well
  pH to 5.7
  0.8% phytoagar
  Autoclave (20 min for a liter, and use slow exhaust)
  After cooling to ~45° C., add
  1× Nitsche & N. vitamins
  1 mg/L zeatin
  500 mg/L carbenicillin or cefataxime
  100 mg/L kanamycin
  Pour into standard petri dishes, put dishes into bag upside down, and store at 4° C.

Shoot Elongation media:
  1× MS basal salt media
  3% sucrose
  Mix well
  pH to 5.7
  0.8% phytoagar
  Autoclave (20 min for a liter, and use slow exhaust)
  After cooling to ~45° C., add
  1× Nitsche & Nitsche vitamins
  0.1 mg/L zeatin
  500 mg/L carbenicillin or cefataxime
  100 mg/L kanamycin
  Pour into sterile magenta boxes, parafilm them, and store at 4° C.

Root media:
  0.5× MS basal salts
  1.5% sucrose
  pH to 5.7
  0.8% phytoagar
  Autoclave (20 min for a liter, and use slow exhaust)
  After cooling to ~45° C., add
  1× Nitsche & Nitsche vitamins
  1 mg/L IBA
  250 mg/L kanamycin
  100 mg/L carbenicillin MSO media:
- 1× MS basal salt media
- Autoclave (20 min for a liter, and use slow exhaust)

MS+media:
- 1× MS basal salt media
- 3% sucrose
- Mix well
- pH to 5.7
- 0.8% phytoagar
- Autoclave (20 min for a liter, and use slow exhaust)
- After cooling to ~45° C., add
- 1× Nitsche & Nitsch vitamins
- 250 mg/L kanamycin
- 100 mg/L carbenicillin
- Pour into sterile magenta boxes, parafilm them, and store at 4° C.

Figure 2:
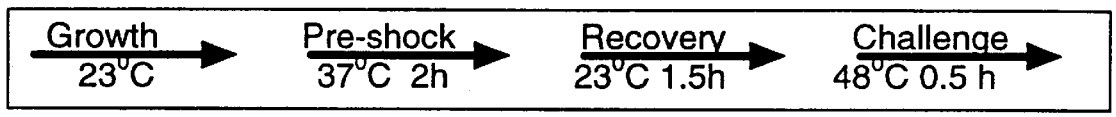
FIG. 2 shows the basic scheme for testing thermotolerance of carrot cells. Callus suspension cultures were routinely maintained for 7 days, at which time 5.0 ml of the suspension was subcultured into 25 ml MS$^+$ without antibiotics contained in 125 mL Erlenmeyer flasks. After 2 days of growth, the cultures were incubated at 37° C. for 2 hours, allowed to recover at room temperature for 1.5 hours, then incubated at 48° C. for 30 minutes. The flasks were then cooled rapidly to room temperature in running water, and incubated with shaking at 23° C. for 14 days.

EXAMPLE 5
Assay for Acquired Thermotolerance of Carrot Cell Cultures:

Cultures were assayed for acquired thermotolerance according to the protocol of Yeh, C.-H., et al., Plant Cell Physiol. 36:1341–48 (1994) with the temperature of the treatment adjusted to reflect the normal thermotolerance of carrot cells. The basic scheme of this test is presented in FIG. 2. Callus suspension cultures were routinely maintained for 7 days, at which time 2.5 ml of suspension was subcultured into 25 ml MS$^+$ without antibiotics contained in 125 mL Erlenmeyer flasks. After 2 days of growth, the cultures were incubated at 37° C. for 2 hours, allowed to recover at room temperature for 1.5 hours, then incubated at 48° C. for 30 minutes. The flasks were then cooled rapidly to room temperature in running water, and incubated with shaking at 23° C. for 14 days. Control cells received the 37° C. pretreatment followed by growth at 23° C. for 14 days. Fresh weight was obtained following collection of the cells by filtration and dry weight was obtained following drying the material on the filter overnight in a vacuum oven at 80° C.

Figure 3:
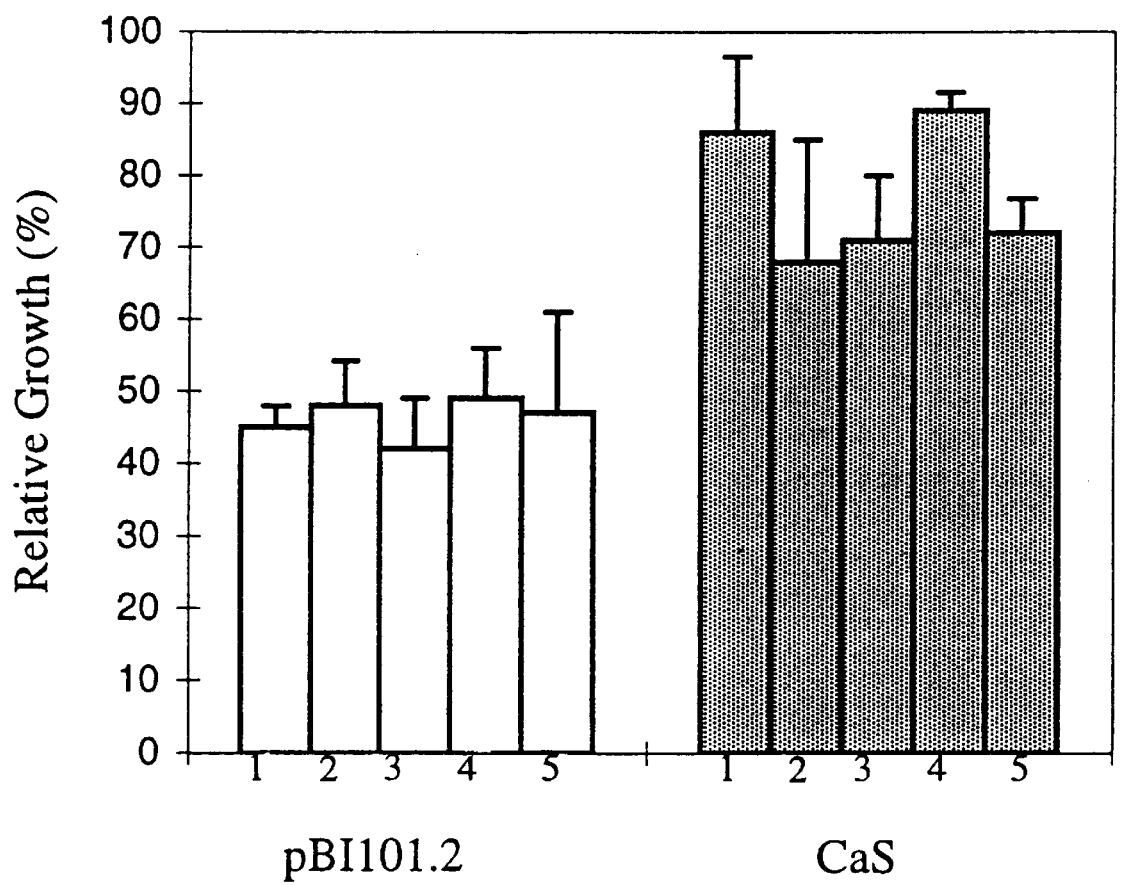
FIG. 3 shows the results of thermotolerance tests for cultured carrot cells, based on measuring growth of a culture (quantified by an increase in dry weight) two weeks after exposure to the thermotolerance regime. Relative growth refers to the growth of the experimentally-treated culture relative to the growth of the same cell line, continuously cultured at room temperature. Each bar on the graph represents the average of three independent experiments and variation in measurements is denoted by the standard error bars.

EXAMPLE 6
Carrot cells containing the CaS construction are more thermotolerant:

Thermotolerance was tested for carrot suspension cultures from five independent vector control-transformed cell lines and five independent Hsp17.7 overexpressor (CaS) transformed cell lines. The results of thermotolerance tests for cultured carrot cells is diagrammed in FIG. 3 and is based on measuring growth of a culture (quantified by an increase in dry weight) two weeks after exposure to the thermotolerance regime. Each bar on the graph represents the average of three independent experiments and variation in measurements is denoted by the standard error bars. Setting the temperature conditions such that the vector control cell lines survive to approximately 50% of untreated cells (i.e. show 50% as much increase in dry weight as the same cell line grown continuously at room temperature which defines the 100% growth in this assay), it is clear that 4 out of 5 CaS lines are significantly more thermotolerant than control cell lines. CaS line 2 was somewhat more variable in its thermotolerance, and its increase in thermotolerance may not be statistically significant. Whole fertile carrot plants have been regenerated from each of these cell lines and these plants have been allowed to self pollinate and to set seed. The thermotolerance of plants grown from these seeds are tested by a variety of assays such as that described below for tomato.

EXAMPLE 7
Thermotolerance testing of transformed tomato plants, Conductivity measurements of control transformed tomatos:

This assay was run essentially according to Binelli, G. and Mascarenhas, J. P., *Developmental Genetics* 11:294–298 (1990), who cite the electrolyte leakage test of Onwueme I. C., *J. Agri. Sci.* Cambridge 92:527–536 (1979) and Chen, H.-H et al., *Crop Sci.* 22:719–725 (1982). The control plants consisted of greenhouse grown *Lycopersicon esculentum* cv. Ailsa Craig growing at an average temperature of about 28° C. and at ambiant daylength. Transformed plants consisted of line 11A8, and were the progeny of a plant derived by the transformation protocol described above using the same construct, pCAS, and Agrobacterium strain used for creating the carrot overexpressing cell lines. These plants were grown under the same conditions as the control plants.

Figure 4:
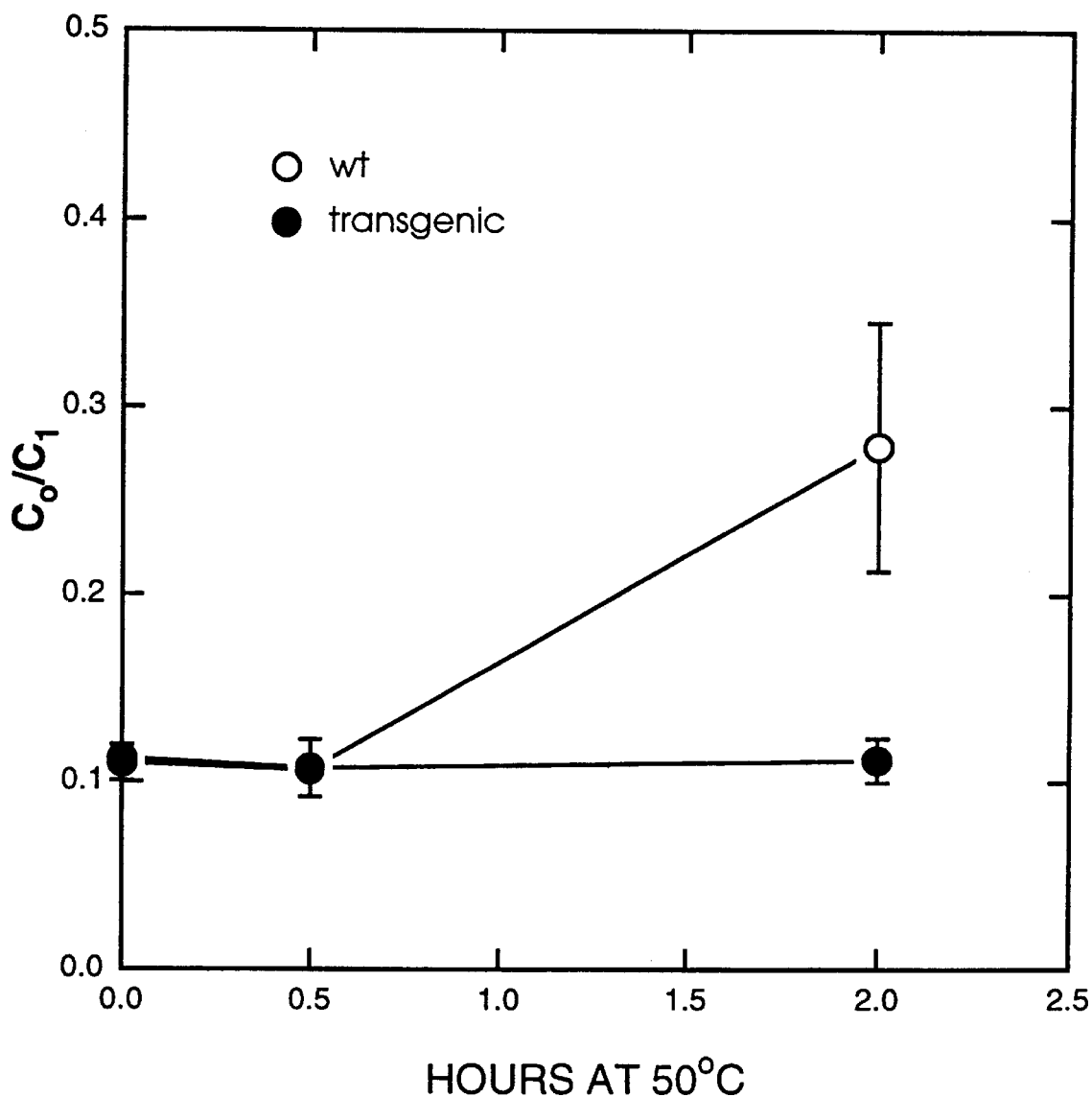
FIG. 4 shows the results of thermotolerance tests for transgenic tomato plants. The transgenic tomato plants engineered to over-express the carrot Hsp 17.7 gene exhibit less cellular damage, assayed by conductivity measurements of electorlyte leakage from cells in response to higher temperature.

Explants (consisting of shoot tips with at least one mature leaf) from plants to be tested were incubated at various temperatures for various periods of time. The standard assay maintained three explants of each plant to be tested at room temperature (25° C.) and three explants of each plant at between 35° C. and 45° C. Humidity was maintained at saturation levels in the incubators used for the higher temperature treatments. At time zero, three leaflets were removed from each explant and 1.5 cm disks cut from each leaflet using a cork borer. Care was taken to avoid major veins and to use leaflets at the same developmental stage. Leaf disks were immediately placed in plastic vials containing 10 ml of water that had been treated by reverse osmosis and then glass-distilled. The vials were capped tightly and placed on a shaker at room temperature for one hour, at which time the conductivity of the solution in each vial was measured. This measurement is $C_0$. The vials were again tightly capped and stored frozen at −80° C. overnight. The vials were defrosted and incubated with shaking at room temperature for one hour, then the conductivity of the solution surrounding the leaf disk was again measured. This measurement is $C_1$. The ratio of $C_0$ to $C_1$ is a measure of membrane leakiness, and a higher value represents increased membrane damage. Samples were removed from explants treated to the various temperatures at time intervals up to about 2 hours, at which time the Ailsa Craig control explants at the higher temperatures were exhibiting severe morphological damage. After two hours at 50° C., the explant from carrot Hsp 17.7 overexpressing tomato plants, did not show any obvious morphological signs of heat damage in three independent experiments. The results are shown in FIG. 4, demonstrating that the transgenic tomato plants engineered to over-express the carrot Hsp 17.7 gene exhibit less cellular damage (assayed by conductivity measurements of cell leakage) in response to higher temperature.

EXAMPLE 8
Enhanced thermotolerance has been achieved and transferred across species lines:

The constitutive over-expression of the carrot Hsp17.7 gene, accomplished by linking the coding sequence of this gene with the 35S CaMV promoter, results in transgenic carrot cells and tomato plants that exhibit significantly increased acquired thermotolerance. This is the first demonstration of enhancement of plant thermotolerance through the over-expression of a low molecular weight heat shock protein. The fact that the enhanced thermotolerance effect can be transferred from one species (carrot) to a completely unrelated species (tomato) is highly significant, since it demonstrates that this gene construct is able to confer enhanced thermotolerance to a wide range of plant species.

EXAMPLE 9

Thermotolerance of regenerated carrot plants and their progeny:

Thermotolerance can be assessed by a variety of measurements in whole plants, including the electolyte leakage assay described for tomato. Several measurements of whole plant physiology are conducted on plants grown from the transgenic carrot seeds in the laboratory, measuring chlorophyll fluorescence, photosynthetic and transpiration rates, increased growth, and nitrogen utilization in the transgenic carrot plants. Similar measurements are done in tomato.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of enhancing thermotolerance in a plant selected from the group consisting of a tomato plant and a carrot plant, comprising the steps of:

transforming a cell or organ of said plant with the Hsp17.7 gene from carrot contained in a vector to produce a transformed cell or organ, wherein said vector further contains a hexterologous promoter capable of expression of said Hsp17.7 gene and other sequences appropriate for successful transcription, translation and expression of said Hsp17.7 gene; and growing said cell or organ into a mature plant or organ.

2. The method of claim 1, wherein said promoter capable of overexpression of said Hsp17.7 gene is CaMV 35S promoter.

3. The method of claim 1, wherein said vector further contains a selection gene.

4. The method of claim 3, wherein said selection gene is selected from the group of kanamycin, carbenicillin and cefotaxime.

5. The method of claim 1, wherein said vector further contains a sequence to allow replication in bacteria and sequences to facilitate integration into a plant genome.

6. The method of claim 1, wherein said vector is pCaS.

7. A plant selected from the group consisting of a tomato plant and a carrot plant transformed with and expressing a heterologous Hsp 17.7 gene.

```
                        SEQUENCE LISTING (1) GENERAL INFORMATION:

(iii) NUMBER OF SEQUENCES:  1

(2) INFORMATION FOR SEQ ID NO:1:

(i) SEQUENCE CHARACTERISTICS:
        (A) LENGTH:  20 bp
        (B) TYPE:  nucleic acid
        (C) STRANDEDNESS:  single-stranded
        (D) TOPOLOGY:  linear (ii) MOLECULE TYPE:
        (A) DESCRIPTION:   other nucleic acid (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:    1:

ATCCTCTCT CGTAAGACAA                                              20
```

8. A plant selected from the group consisting of a tomato plant and a carrot plant transformed with and expressing a Hsp 17.7 gene from carrot under the transcriptional activity of heterologous promoter.

9. The plant of claim 8, wherein transcription of said Hsp 17.7 gene from carrot is controlled by a promoter, wherein said promoter is capable of expression of said Hsp 17.7 gene from carrot.

10. The plant of claim 8, wherein a vector containing said Hsp 17.7 gene from carrot is used to transform said plant, wherein said vector further contains a selection gene.

11. The plant of claim 10, wherein said vector containing Hsp 17.7 gene from carrot further contains a sequence to allow replication in bacteria and sequences to facilitate integration into a genome of said plant.

* * * * *